United States Patent
Gill

(10) Patent No.: US 8,657,887 B2
(45) Date of Patent: Feb. 25, 2014

(54) PROSTHESIS COVERING

(75) Inventor: Hugh Gill, Midcalder (GB)

(73) Assignee: Tough EMAS Limited, Livingston (GB)

( * ) Notice: Subject to any disclaimer, the term of this patent is extended or adjusted under 35 U.S.C. 154(b) by 338 days.

(21) Appl. No.: 12/921,635

(22) PCT Filed: Mar. 13, 2009

(86) PCT No.: PCT/GB2009/050248
§ 371 (c)(1),
(2), (4) Date: Oct. 5, 2010

(87) PCT Pub. No.: WO2009/115835
PCT Pub. Date: Sep. 24, 2009

(65) Prior Publication Data
US 2011/0054636 A1 Mar. 3, 2011

(30) Foreign Application Priority Data

Mar. 17, 2008 (GB) .................................. 0804933.0
Jun. 9, 2008 (GB) .................................. 0810519.9

(51) Int. Cl.
*A61F 2/54* (2006.01)
*A41D 19/00* (2006.01)

(52) U.S. Cl.
USPC ............................................. 623/57; 2/164

(58) Field of Classification Search
CPC ................. A61F 2002/5001; A41D 19/0006; A41D 19/001; A41D 19/0068; A41D 19/01576
USPC ..................................................... 2/164, 168
See application file for complete search history.

(56) References Cited

U.S. PATENT DOCUMENTS

| | | | |
|---|---|---|---|
| 2,508,156 A | 5/1950 | Gillman | |
| 4,197,592 A * | 4/1980 | Klein | 2/161.1 |
| 5,020,162 A * | 6/1991 | Kersten et al. | 2/164 |
| 5,133,775 A | 7/1992 | Chen | |
| 5,387,245 A * | 2/1995 | Fay et al. | 623/37 |
| 5,498,472 A * | 3/1996 | Gold | 428/102 |
| 6,175,962 B1 * | 1/2001 | Michelson | 2/161.7 |
| 7,316,795 B1 | 1/2008 | Knauss | |
| 2005/0101693 A1 | 5/2005 | Arbogast et al. | |

FOREIGN PATENT DOCUMENTS

| | | |
|---|---|---|
| GB | 2067074 A | 7/1981 |
| WO | WO-03/017877 A1 | 3/2003 |
| WO | WO-2006/110790 A2 | 10/2006 |

OTHER PUBLICATIONS

Lager, Johan, "International Search Report", for PCT/GB2009/050248 as mailed Jun. 30, 2009, 4 pages.

* cited by examiner

*Primary Examiner* — David H Willse
(74) *Attorney, Agent, or Firm* — K&L Gates LLP

(57) ABSTRACT

A prosthesis covering comprising an outer layer having an exterior surface defining an outermost surface of a prosthesis; and an inner layer having an interior surface that lies adjacent the prosthesis when the prosthesis covering is on the prosthesis. The outer layer defines a space in which the inner layer is received such that an inwardly directed surface of the outer layer lies adjacent an outwardly directed surface of the inner layer. The inwardly directed surface of the outer layer and the outwardly directed surface of the inner layer are attached to each other at a plurality of spaced apart locations, the inwardly directed surface of the outer layer and the outwardly directed surface of the inner layer elsewhere being unattached to each other.

34 Claims, 4 Drawing Sheets

PROSTHESIS COVERING

FIELD OF THE INVENTION

The present invention relates to a prosthesis covering and a method of forming the same. In particular but not exclusively the invention relates to a prosthesis covering for an upper body prosthesis, such as a prosthetic hand.

BACKGROUND TO THE INVENTION

It is known to form coverings for prostheses, such as prosthetic hands, from materials such as silicone rubber. A prosthesis covering provides for protection of the prosthesis during use and may also be crafted to provide a cosmetic effect for the user of the prosthesis. Known techniques for forming prosthesis coverings from silicone rubber include rotational "slush moulding" and paste "pack" moulding using three part moulds.

The present inventor has appreciated known prosthesis coverings to have shortcomings. Accordingly, it is an aim for the present invention to provide an improved prosthesis covering and a method of forming the same. It is a further aim for the present invention to provide a prosthesis covering configured to cover a prosthesis of a kind that has at least two parts that, in use, move in relation to each other, such as a prosthetic hand having movable digits.

STATEMENT OF INVENTION

According to a first aspect of the invention there is provided a prosthesis covering comprising:
- an outer layer having an exterior surface that defines an outermost surface when the prosthesis covering is in use on the prosthesis;
- an inner layer having an interior surface that lies adjacent the prosthesis when the prosthesis covering is in use on the prosthesis;
- the outer and inner layers having generally a same form and the outer layer defining a space in which the inner layer is received such that an inwardly directed surface of the outer layer lies adjacent an outwardly directed surface of the inner layer; and
- the inwardly directed surface of the outer layer and the outwardly directed surface of the inner layer being attached to each other at a plurality of spaced apart locations, the inwardly directed surface of the outer layer and the outwardly directed surface of the inner layer elsewhere being unattached to each other.

The attachment of the outer and inner layers to each other at a plurality of discrete, spaced apart locations with the outer and inner layers elsewhere (e.g. in between the spaced apart locations of attachment) being unattached to each other can provide for an improvement in longevity of the prosthesis covering when in use. This is because the outer layer can move without movement of the inner layer and vice-versa during use of the prostheses, which can reduce strain on and hence wear of the prosthesis covering. The present invention may be applied to advantageous effect in a covering for a prosthesis having moving parts in which the moving parts strain the covering.

More specifically, the prosthesis covering may be configured to cover a prosthesis having at least two moving parts, such as a prosthetic hand or foot. Thus, the prosthesis covering may have the form of a glove. The covering in the form of a glove may be for covering a prosthetic hand having movable digits, which may, for example, be driven by motors in the prosthetic hand. The covering in the form of a glove may be configured to cover individual digits of a prosthetic hand. More specifically, the covering in the form of a glove may comprise a plurality of sheaths each of which is configured to receive a respective digit. In use, the present invention may provide for a reduction in the load borne by a motor when driving a digit because the motor may have to work against the resistance to movement presented by the inner layer but not the outer layer, the inner layer being capable of moving without the outer layer moving with it.

More specifically, the inner and outer layers may be unattached to each other in the vicinity of a location where the prosthetic covering is configured to cover a joint of the prosthesis, e.g. a knuckle of a prosthetic hand.

Alternatively or in addition, the inner and outer layers may be attached to each other at locations spaced apart from parts of the prosthesis covering that flex during use of the prosthesis covering on a prosthesis.

Alternatively or in addition, the inner and outer layers may be attached to each other at at least one location towards a first end (e.g. proximal end) of the prosthetic covering and at at least one location towards an opposing, second end (e.g. distal end) of the prosthetic covering. More specifically, the inner and outer layers may be unattached to each other between the first and second ends of the prosthetic covering.

Alternatively or in addition and where the prosthetic covering is configured to cover a prosthetic hand, the inner and outer layers may be attached to each other at a wrist location of the prosthetic covering Alternatively or in addition and where the prosthetic covering is configured to cover a prosthetic hand, the inner and outer layers may be attached to each other at at least one finger tip location of the prosthetic covering.

Alternatively or in addition, the outer and inner layers may be formed of different materials. For example, the outer layer may be formed of a water-proof material and the inner layer may be formed of a water pervious material.

More specifically, one of the outer and inner layers may be formed at least in part of an elastomer and the other of the outer and inner layers may be formed at least in part of a textile.

Alternatively or in addition, the outer layer may be formed at least in part of an elastomer.

More specifically, the elastomer may comprise silicone rubber.

More specifically, the silicone rubber may comprise at least one of: a tin-based silicone rubber, such as Repsil™ T; and a platinum-based silicone rubber, such as from the Smooth-On Platinum Silicones series.

Alternatively or in addition, the outer layer may have a Shore A hardness of between substantially 10 and substantially 40.

More specifically, the outer layer may have a Shore A hardness of between substantially 20 and substantially 30.

More specifically, the outer layer may have a Shore A hardness of substantially 25.

Alternatively or in addition, the outer layer may be one of transparent and translucent.

Alternatively or in addition, the outer layer may have a thickness (from the inwardly directed surface to the exterior surface) of between substantially 1 mm and substantially 2 mm.

More specifically, the outer layer may have a thickness of substantially 1.5 mm.

Alternatively or in addition, the inner layer may be formed at least in part of a textile.

Alternatively or in addition, the inner layer may comprise a spandex material, such as Lycra™.

More specifically, the inner layer may comprise substantially 4% to substantially 12% Lycra™. More specifically the inner layer may comprise substantially 8% Lycra™ to 12% Lycra™. Substantially 8% to substantially 12% Lycra™ has been found to provide superior performance as regards ability to stretch and integrity of the inner layer when in use. More specifically, the inner layer may comprise substantially 8% Lycra™, which has been found to have appropriate properties for certain applications.

Alternatively or in addition, the inner layer may have a pitch of (e.g. be knitted as) substantially 591 needles per meter (15 needles to the inch).

The spandex material can provide for stretching of the inner layer. For example, where the inner layer is for a prosthetic hand, the stretchability of the spandex material provides for ease of flexing of the inner layer in the region of moveable joints of the prosthetic hand.

Alternatively or in addition, the inner layer may comprise nylon. The nylon may provide for a degree of stretching of the inner layer. More particularly, the nylon can allow the inner layer to conform to a surface profile of whatever the inner layer covers, e.g. a prosthetic hand.

Alternatively or in addition, the inner layer may be unitary. More specifically, the inner layer may be seamless, i.e. formed of one piece of material.

Alternatively or in addition, the inner layer may have a thickness of substantially 0.6 mm.

Alternatively or in addition, the prosthesis covering may comprise an adhesive which attaches the inner and outer layers to each other at the plurality of spaced apart locations.

More specifically, the adhesive may comprise a silicone adhesive.

Alternatively or in addition, the adhesive may comprise a one component adhesive.

Alternatively or in addition, at least one of the inner layer and the outer layer may be coated with an adhesive resistant material at locations where the outer and inner layers are unattached to each other.

More specifically, the adhesive resistant material may comprise at least one of PVC and a silicone release agent.

Alternatively or in addition and where the inner layer is formed of a textile the inner layer may be coated with the adhesive resistant material. Thus, the adhesive resistant material may prevent the adhesive penetrating the textile. Penetration of the textile with adhesive at locations other than where the outer and inner layers are attached may cause the inner layer to become stiffer; this may, for example, increase the resistance presented by the inner layer to a motor which is driving a digit of the prosthesis covered by the inner layer.

In a form in which the outer and inner layers are formed of different materials, the inner layer may comprise at least one element formed of the material of the outer layer, the at least one element being attached to the outwardly directed surface of the inner layer at a location where the outer and inner layers are unattached to each other. The at least one element can provide for increased friction between the inner and outer layers. For example, where the at least one element is provided on a digit portion of the inner layer of a covering for a prosthetic hand, the increased friction can reduce movement, such as rotation about the digit, of the outer layer in relation to the inner layer.

More specifically, the inner layer may comprise a plurality of elements attached to the outwardly directed surface of the inner layer at spaced apart locations. For example, the plurality of elements may be spaced apart along a digit portion of the inner layer of a covering for a prosthetic hand.

Alternatively or in addition, where the outer layer is formed of an elastomer and the inner layer is formed of a textile, the at least one element may be formed of an elastomer.

Alternatively or in addition, the prosthesis covering may comprise an intermediate layer between the inner and outer layers. In use, the intermediate layer may make the prosthesis covering more robust.

More specifically and where the prosthesis covering is for a prosthetic hand, the intermediate layer may cover and may extend no further than at least one finger or thumb of the covering.

Alternatively or in addition and where the prosthesis covering is configured to cover a joint of the prosthesis (e.g. a knuckle of a prosthetic hand), the intermediate layer may extend no further than an area adjacent the joint of the prosthesis. Thus, the intermediate layer may make the prosthesis covering more robust where the prosthesis covering is liable to be subject to wear.

Alternatively or in addition, the intermediate layer may be configured such that, in use, it encircles a part, such as at least one finger, of the prosthesis.

Alternatively or in addition, the intermediate layer may comprise at least one of a polymer, such as PVC, and a textile.

More specifically, where the intermediate layer comprises a textile, the textile may be formed of at least one of an aramid fibre and lycra.

Alternatively or in addition, where the intermediate layer comprises a textile and the inner layer comprises a textile, the intermediate layer and the inner layer may be joined together, e.g. by stitching.

Alternatively or in addition, where the intermediate layer comprises an aramid fibre the intermediate layer may be joined to at least one of the inner layer and the outer layer by means of silicone adhesive.

Alternatively or in addition, where the intermediate layer comprises a polymer, the intermediate layer may be disposed on the inner layer. Where the inner layer is formed of a textile, the inner layer may have a smaller pitch where the intermediate layer is present than elsewhere. Alternatively or in addition, where the inner layer is formed of a textile, interstices in the textile may be filled by silicon rubber, the intermediate layer being disposed above the silicone rubber. Thus, the polymeric intermediate layer may sit on a surface of the textile.

According to a second aspect of the present invention, there is provided a prosthesis comprising a prosthesis covering according to the first aspect of the present invention.

More specifically, the prosthesis may be a prosthetic hand.

Further embodiments of the second aspect of the present invention may comprise one or more features of the first aspect of the present invention.

According to a third aspect of the present invention, there is provided a method of forming a prosthetic covering, the method comprising the steps of:

forming an outer layer having an exterior surface that defines an outermost surface of a prosthesis when the prosthesis covering is in use on the prosthesis;

forming an inner layer having an interior surface that lies adjacent the prosthesis when the prosthesis covering is in use on the prosthesis;

the outer and inner layers being formed such that they have generally a same form and such that the outer layer defines a space;

receiving the inner layer in the space defined by the outer layer and such that an inwardly directed surface of the outer layer lies adjacent an outwardly directed surface of the inner layer; and attaching the inwardly directed surface of the outer layer and the outwardly directed surface of the inner layer to each other at a plurality of spaced apart locations, the inwardly directed surface of the outer layer and outwardly directed surface of the inner layer elsewhere being unattached to each other.

More specifically, the step of attaching the outer and inner layers to each other may comprise applying adhesive to adjacent surfaces of the inner and outer layers.

More specifically, the step of attaching the outer and inner layers may comprise forming a bore in the outer layer at a location at which the inner and outer layers are to be attached and injecting the adhesive through the bore. Where the adhesive comprises a silicone adhesive and the outer layer is formed of silicone rubber, the adhesive may seal the bore after injection of adhesive through the bore.

Alternatively or in addition, the method may further comprise disposing the inner layer on a support, such as a mandrel.

More specifically, the method may further comprise disposing the outer layer over the inner layer on the support before attaching the outer and inner layers to each other at the plurality of spaced apart locations.

Alternatively or in addition, the method may comprise disposing, e.g. by spraying or painting, an adhesive resistant material on the outwardly directed surface of the inner layer at locations where the outer and inner layers are to be unattached to each other, the step of disposing the adhesive resistant material being carried out before the step of receiving the inner layer in the space defined by the outer layer.

Further embodiments of the third aspect of the present invention may comprise one or more features of any previous aspect of the present invention.

According to a further aspect of the invention there is provided a prosthesis covering comprising:
an outer layer having an exterior surface which defines an outermost surface of a prosthesis when the prosthesis covering is in use on the prosthesis;
an inner layer having an interior surface that lies adjacent the prosthesis when the prosthesis covering is in use on the prosthesis; and
the outer layer defining a space in which the inner layer is received such that an inwardly directed surface of the outer layer lies adjacent an outwardly directed surface of the inner layer.

More specifically, the outer and inner layers may have generally a same form.

Alternatively or in addition, the outer and inner layers may be attached to each other at a plurality of spaced apart locations, the outer and inner layers elsewhere being unattached to each other.

Further embodiments of the further aspect of the present invention may comprise one or more features of any other aspect of the present invention.

The inventors have appreciated the feature of the intermediate layer to be of wider applicability than hitherto described. Thus, according to a yet further aspect of the present invention there is provided a prosthesis covering comprising:
an outer layer having an exterior surface which defines an outermost surface of a prosthesis when the prosthesis covering is in use on the prosthesis;
an inner layer having an interior surface that lies adjacent the prosthesis when the prosthesis covering is in use on the prosthesis;
the outer and inner layers having generally a same form and the outer layer defining a space in which the inner layer is received such that an inwardly directed surface of the outer layer lies adjacent an outwardly directed surface of the inner layer; and
an intermediate layer lying between the inner and outer layers, the intermediate layer being configured such that, in use, the intermediate layer encircles a part of the prosthesis.

More specifically, the inwardly directed surface of the outer layer and the outwardly directed surface of the inner layer being may be attached to each other at a plurality of spaced apart locations, the outwardly directed and inwardly directed surfaces elsewhere being unattached to each other.

Further embodiments of the yet further aspect of the present invention may comprise one or more features of any other aspect of the present invention.

BRIEF DESCRIPTION OF THE DRAWINGS

The present invention will now be described by way of example only with reference to the following drawings, of which.

SPECIFIC DESCRIPTION

Figure 1:
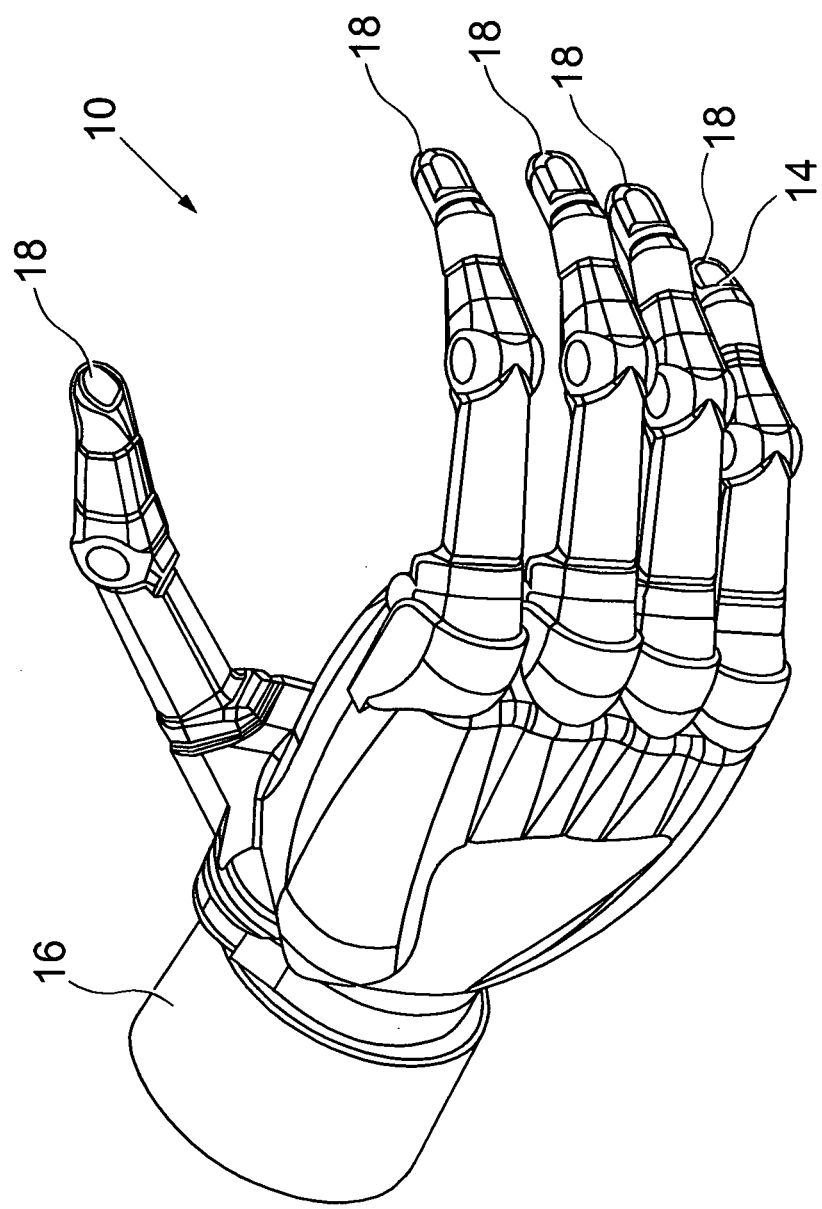
FIG. 1 is a perspective view of a prosthesis covering according to the present invention.

FIG. 1 provides a perspective view of a prosthesis covering 10 according to the present invention. As can be seen from FIG. 1, the prosthesis covering 10 is in the form of a glove and is thus for covering a full prosthetic hand (not shown).

Figure 2:
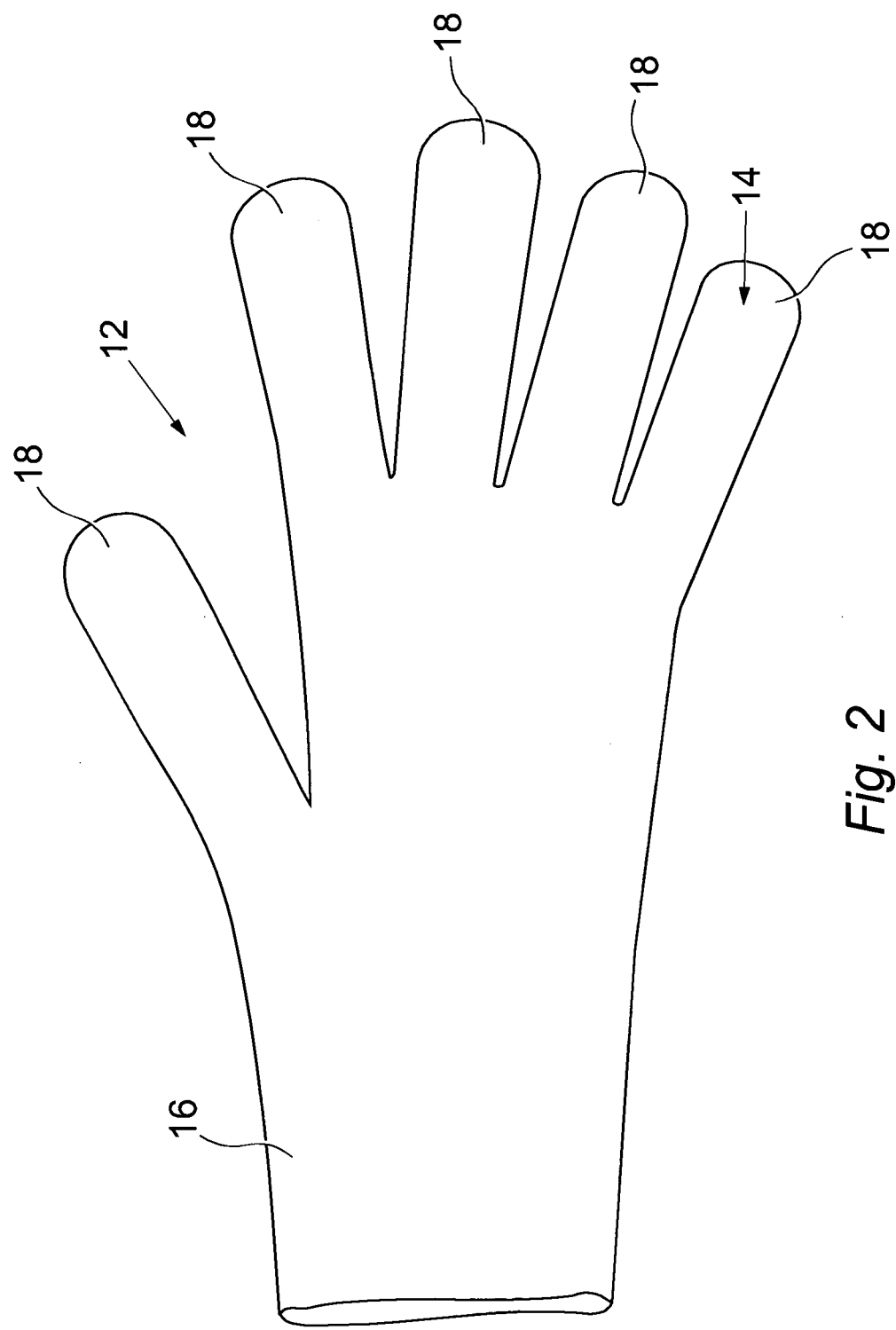
FIG. 2 is a view of the inner layer of the prosthesis covering of FIG. 1.

FIG. 2 provides a plan view of the inner layer 12 of the prosthesis covering 10 shown in FIG. 1.

Figure 3:
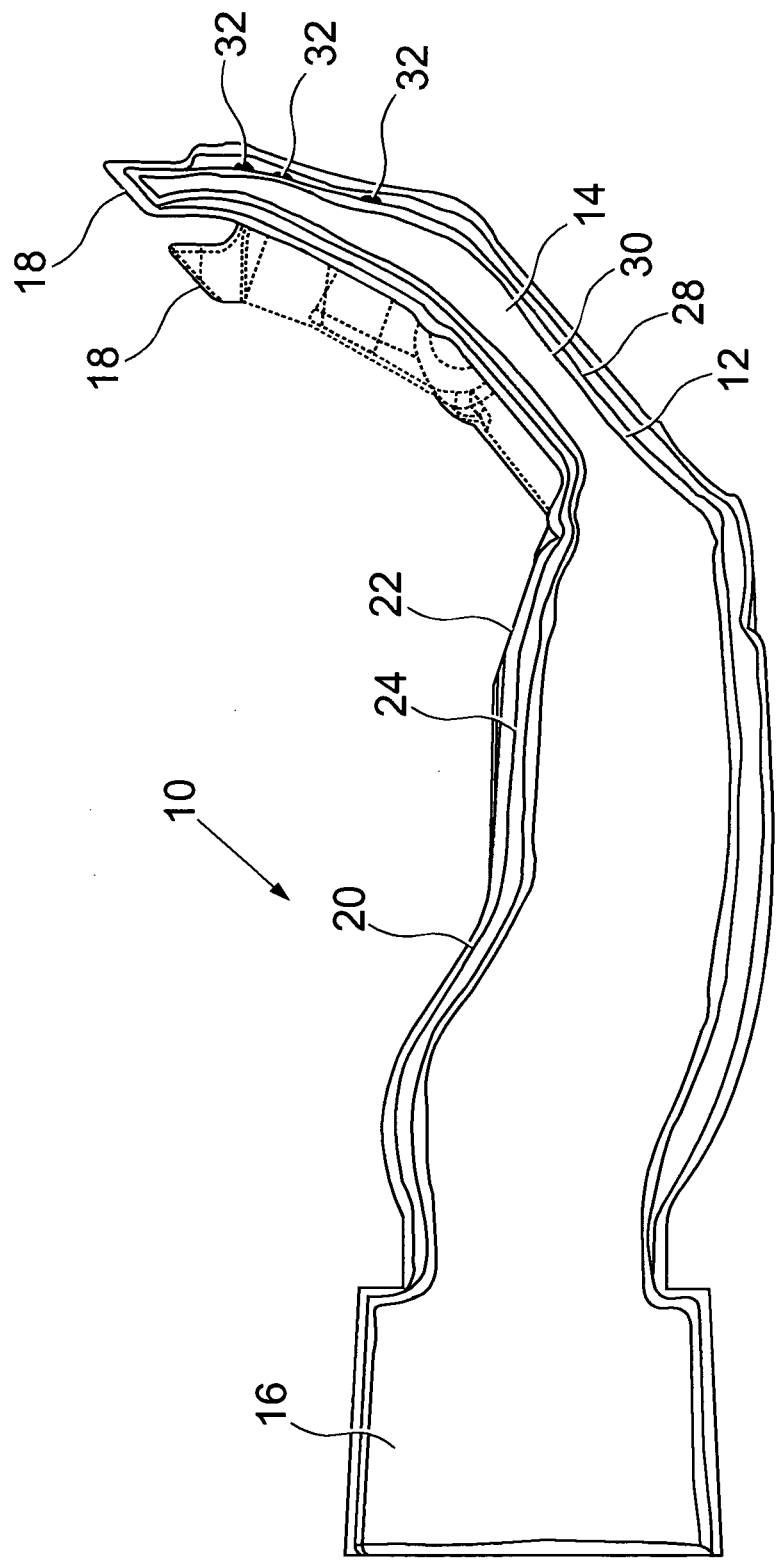
FIG. 3 is a view in cross section though the prosthesis covering of FIG. 1.

FIG. 3 shows the prosthesis covering of FIG. 1 in cross-section though the little finger 14. The prosthesis covering 10 comprises an outer layer 20, which has an exterior surface 22 and an inwardly directed surface 24, and the inner layer 12, which has an outwardly directed surface 28 and an interior surface 30. The inner layer 12 is formed of 92% nylon and 8% Lycra™. The nylon and Lycra are woven with a pitch of substantially 591 needles per meter (15 needles per inch). The inner layer comprises three elements 32 formed of silicone rubber; the three elements are spaced apart from each other along the digit portion of the prosthesis covering and are attached to the outwardly directed surface 28 of the inner layer 12.

Referring to both FIG. 1 and FIG. 3, the outer and inner layers 20, 12 are attached to each other at a wrist portion 16 and finger tip 18 portions of the prosthesis covering 10 by means of a one component silicone adhesive, namely Renew Silicone Adhesive supplied by Renew Inc., 95 W. Main St. Suite 5117, Chester, N.J. 07930, USA. Elsewhere the outer and inner layers 20, 12 are unattached to each other.

The prosthesis covering 10 of FIGS. 1 and 3 is formed as follows. The outer layer 20 and the inner layer 12 are formed separately. The outer layer 20 is formed by one of two methods as described immediately below.

According to the first method, the outer layer 20 is formed by the well known injection moulding process. Repsil™ T silicone rubber supplied by WP Notcutt, Homewood Farm, Newark lane, Ripley, Surrey GU23 6DJ is the moulded material. An unpolished injection moulding tool produces a translucent outer layer. A transparent outer layer, which is often preferred, is produced by a polished injection moulding tool. A transparent outer layer is often preferred because the inner layer can be printed with a design or dyed and the transparent property of the outer layer allows the inner layer to be seen.

According to the second method, the outer layer 20 is formed by means of a vacuum casting process. A platinum-based silicone rubber from the Smooth-On Platinum Silicones series is used as the cast material. The Smooth-On Platinum Silicones series is supplied by Smooth-On, Inc., 2000 Saint John Street, Easton, Pa. 18042, USA. The first step in the second method is the pouring of the silicone rubber onto a rotating mandrel; the mandrel may be coated with a silicone release agent to ease removal of the outer layer from the mandrel when the outer layer is formed. Rotation of the mandrel provides for even distribution of the silicone rubber over the mandrel. The poured silicone rubber is allowed to part cure. During part curing of the silicone rubber the mandrel is rotated to maintain an even distribution of silicone rubber. The silicone rubber is part cured when the silicone rubber is less liable to tear or split on handling but is sufficiently uncured at its surface to permit a pattern to be impressed in it.

Irrespective of which of the two methods is used, the silicone rubber has a composition such that the outer layer has a Shore A hardness of substantially 25 when formed. Also, the outer layer has a thickness of substantially 1.5 mm.

A mould is then fitted over the silicone rubber. The mould has a pattern formed on its inside surface. The pattern comprises surface features such as wrinkles and finger prints. The pattern is formed on the mould by well known means. The mould is formed of silicone rubber; either a platinum-based or a tin-based silicone rubber may be used for the mould. Before fitting of the mould over the silicone rubber a release substance is applied as a thin coating to one, other or both of the mould and the silicone rubber surface that will come into contact with the mould. The release substance comprises vaseline in a solvent, which is painted onto surfaces to be coated. Alternatively, surfaces to be coated are dipped into the release substance.

When the mould is in position, a vacuum is applied to the inside of the mould by known means to pull the inside surface of the mould against the surface of the silicone rubber. Thus, the pattern on the mould is impressed upon the surface of the silicone rubber. The mould is kept in position such that it is pulled against the surface of the silicone rubber for between about thirty minutes and about forty-five minutes. The vacuum is then released so that the mould is no longer pulled against the silicone rubber. The mould is kept in place over the silicone rubber for about one hour, which is normally a sufficient period of time to allow the silicone rubber to cure properly. This provides for a matt finish to the silicone rubber. The mould is then removed from the mandrel and the now formed covering is removed from the mandrel.

The unitary inner layer 12 is formed by a well known knitting process and the silicone rubber elements 32 formed by depositing uncured silicone rubber paste or liquid where required on the outwardly directed surface 28 of the inner layer. The silicone rubber elements are allowed to cure for 15 minutes. The inner layer is sprayed with PVC or a silicone rubber release agent at locations where the inner and outer layers are to remain unattached to each other. The unitary inner layer 12 has a thickness of substantially 0.6 mm. The inner layer 12 is then placed on a mandrel (not shown).

The cured outer layer 20 is then fitted over the inner layer 12; the outer layer having been formed by one of the two methods described above. A bore is formed in each finger tip of the outer layer, e.g. by means of a needle or like implement. Sufficient adhesive to attach the inwardly directed surface of the outer layer to the outwardly directed surface of the inner layer in the finger tip region is injected through each bore. The adhesive is allowed to cure for 15 minutes to effect attachment of the outer and inner layers at the finger tips. Adhesive remaining in each bore after the injection process cures and seals the bore.

The wrist portion 16 of the outer layer 20 is peeled back and adhesive is deposited on the inwardly directed surface of the wrist portion of the outer layer in two generally parallel lines extending around the wrist. The wrist portion is then folded back onto the wrist portion of the inner layer 12 and the wrist portions of the outer and inner layers clamped together for 15 minutes to effect their attachment. The prosthesis covering 10 is then removed from the mandrel for fitting to a prosthetic hand.

Figure 4A:
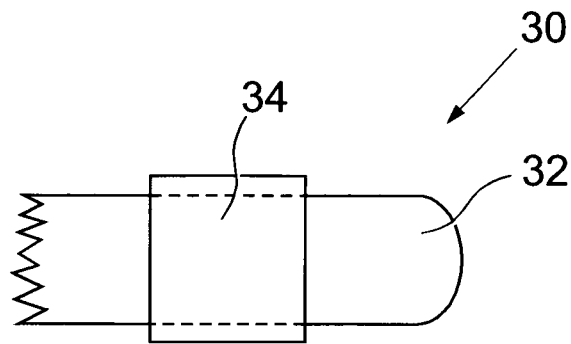
FIGS. 4A to 4C provide partial views of alternative embodiments of covering having an intermediate layer.

FIG. 4A shows a finger 30 of a prosthesis covering according to the present invention. The outer layer of the finger 30 is not shown in FIG. 4A. A sleeve 34 (which constitutes an intermediate layer) of an aramid fibre (such as from Turtleskin of Warwick Mills, 301 Turnpike Road, P O Box 409, New Ipswich, N.H. 03071, USA) is provided over the knuckle area of the finger 30. The sleeve is joined to the outwardly directed surface of the inner layer by means of a one component silicone adhesive. In another form, the sleeve may be joined to the inwardly directed surface of the outer layer by means of a one component silicone adhesive.

Figure 4B:
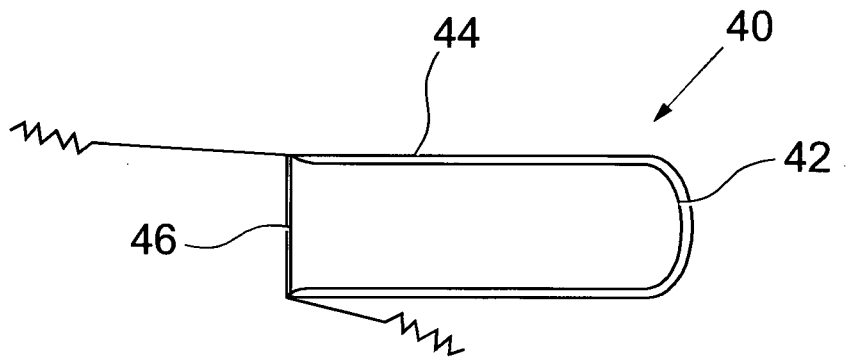
Figure 4C:
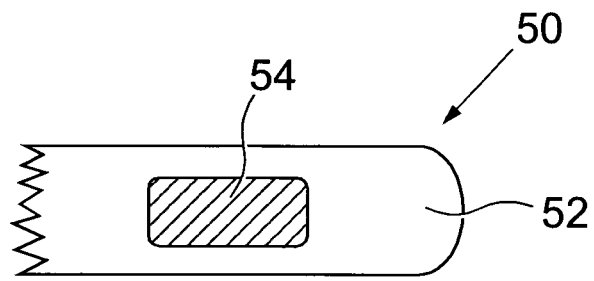

FIG. 4B shows a finger 40 of a prosthesis covering according to the present invention. The outer layer of the finger 40 is not shown in FIG. 4B. An intermediate layer 44 is formed by doubling up the lycra material of the inner layer 42, such that the intermediate layer terminates at the base of the finger. The inner layer 42 and the intermediate layer 44 are joined at the base by stitching 46.

FIG. 4B shows a finger 50 of a prosthesis covering according to the present invention. The outer layer of the finger 50 is not shown in FIG. 4B. A layer of PVC 54 (which constitutes an intermediate layer) is present on the outer surface of the inner layer 52. The layer of PVC 54 is deposited on the inner layer by screen printing. Before screen printing, either the pitch of the inner layer is decreased where the PVC is to be deposited or soft silicone rubber is used to fill the interstices of the inner layer to reduce an extent to which the PVC is absorbed by the inner layer.

The invention claimed is:

1. A prosthesis covering having an appendage joining portion, fingers, and finger tips, and having a dorsal side and a palmar side, the covering comprising:

an outer layer having an exterior surface that defines an outermost surface of a prosthesis when the prosthesis covering is in use on the prosthesis;

an inner layer having an interior surface that lies adjacent the prosthesis when the prosthesis covering is in use on the prosthesis;

the outer and inner layers having generally a same form and the outer layer defining a space in which the inner layer is received such that an inwardly directed surface of the outer layer lies adjacent an outwardly directed surface of the inner layer; and the inwardly directed surface of the outer layer and the outwardly directed surface of the inner layer of the entire covering being attached to each other solely at the finger tips and the appendage joining portion of the prosthesis covering, the inwardly directed surface of the outer layer and the outwardly directed surface of the inner layer of the prosthesis cover elsewhere being unattached to each other, whereby motion of the inner layer and outer layer relative to each other is not impeded thereby not restricting the flexion of the fingers of the prosthesis, and wherein the exterior surface of the outer layer is configured to resemble human skin.

2. A prosthesis covering according to claim 1, wherein in which the prosthesis covering is configured to cover a prosthesis having at least two parts that move in relation to each other.

3. A prosthesis covering according to claim 2, wherein the prosthesis covering has the form of a glove for covering a prosthetic hand having movable digits.

4. A prosthesis covering according to claim 2, wherein the inner and outer layers are unattached to each other in the vicinity of a location where the prosthetic covering is configured to cover a joint of the prosthesis.

5. A prosthesis covering according to claim 1, wherein the outer and inner layers are formed of different materials.

6. A prosthesis covering according to claim 5, wherein one of the outer and inner layers is formed at least in part of an elastomer and the other of the outer and inner layers is formed at least in part of a textile.

7. A prosthesis covering according to claim 1, wherein the outer layer is formed at least in part of an elastomer.

8. A prosthesis covering according to claim 7, wherein the elastomer comprises silicone rubber.

9. A prosthesis covering according to claim 1, wherein the outer layer has a Shore A hardness of between substantially 20 and substantially 30.

10. A prosthesis covering according to claim 1, wherein the inner layer comprises a spandex material.

11. A prosthesis covering according to claim 1, wherein the inner layer comprises nylon.

12. A prosthesis covering according to claim 1, wherein the inner layer is unitary.

13. A prosthesis covering according to claim 1, wherein at least one of the inner layer and the outer layer is coated with an adhesive resistant material at locations where the outer and inner layers are unattached to each other.

14. A prosthesis covering according to claim 1, wherein the inner layer is formed of a textile, in which the inner layer is coated with an adhesive resistant material.

15. A prosthesis covering according to claim 1, wherein the outer and inner layers are formed of different materials, and wherein the inner layer comprises at least one element formed of the material of the outer layer, the at least one element being attached to the outwardly directed surface of the inner layer at a location where the outer and inner layers are unattached to each other.

16. A prosthesis covering according to claim 15, wherein the inner layer comprises a plurality of elements attached to the outwardly directed surface of the inner layer at spaced apart locations.

17. A prosthesis covering according to claim 15, wherein the outer layer is formed of an elastomer and the inner layer is formed of a textile, in which the at least one element is formed of an elastomer.

18. A prosthesis covering according to claim 1, wherein the prosthesis covering comprises an intermediate layer between the inner and outer layers.

19. A prosthesis covering according to claim 18, wherein the prosthesis covering is for a prosthetic hand, and wherein in which the intermediate layer covers and extends no further than at least one digit of the covering.

20. A prosthesis covering according to claim 18, wherein the prosthesis covering is configured to cover a joint of the prosthesis, and wherein the intermediate layer extends no further than an area adjacent the joint of the prosthesis.

21. A prosthesis covering according to claim 18, wherein the intermediate layer is configured such that, in use, it encircles a part of the prosthesis.

22. A prosthesis covering according to claim 18, wherein the intermediate layer comprises at least one of a polymer and a textile.

23. A prosthesis covering according to claim 18, wherein the intermediate layer comprises a textile, and wherein the textile is formed of at least one of an aramid fibre and lycra.

24. A prosthesis covering according to claim 18, wherein the intermediate layer comprises a textile and the inner layer comprises a textile, and wherein the intermediate layer and the inner layer are joined together.

25. A prosthesis covering according to claim 18, wherein the intermediate layer comprises an aramid fibre, and wherein the intermediate layer is joined to at least one of the inner layer and the outer layer by means of silicone adhesive.

26. A prosthesis covering according to claim 18, wherein the intermediate layer comprises a polymer, and wherein the intermediate layer is disposed on the inner layer.

27. A prosthesis comprising:
a prosthesis covering having a dorsal side and a palmar side, the prosthesis covering comprising:
an appendage joining portion, fingers, and finger tips,
an outer layer having an exterior surface that defines an outermost surface of a prosthesis when the prosthesis covering is in use on the prosthesis;
an inner layer having an interior surface that lies adjacent the prosthesis when the prosthesis covering is in use on the prosthesis;
the outer and inner layers having generally a same form and the outer layer defining a space in which the inner layer is received such that an inwardly directed surface of the outer layer lies adjacent an outwardly directed surface of the inner layer; and
the inwardly directed surface of the outer layer and the outwardly directed surface of the inner layer of the entire covering being attached to each other solely at two spaced apart locations, the inwardly directed surface of the outer layer and the outwardly directed surface of the inner layer of the prosthesis cover elsewhere being unattached to each other,
wherein one of said spaced apart locations is at the appendage joining portion and another one of said spaced apart locations is at the fingertips,
whereby motion of the inner layer and outer layer relative to each other is not impeded thereby not restricting the flexion of the fingers of the prosthesis, and
wherein the exterior surface of the outer layer is configured to resemble human skin.

28. A prosthesis according to claim 27, wherein the prosthesis is a prosthetic hand.

29. A method of forming a prosthetic covering having an appendage joining portion, fingers, and finger tips and a dorsal side and a palmar side, the method comprising the steps of:
forming an outer layer having an exterior surface that defines an outermost surface of a prosthesis when the prosthesis covering is in use on the prosthesis;

forming an inner layer having an interior surface that lies adjacent the prosthesis when the prosthesis covering is in use on the prosthesis;

the outer and inner layers being formed such that they have generally a same form and such that the outer layer defines a space;

receiving the inner layer in the space defined by the outer layer and such that an inwardly directed surface of the outer layer lies adjacent an outwardly directed surface of the inner layer; and attaching the inwardly directed surface of the outer layer and the outwardly directed surface of the inner layer to each other solely at the finger tips and the appendage joining portion of the prosthesis covering, the inwardly directed surface of the outer layer and the outwardly directed surface of the inner layer elsewhere on the prosthesis covering being unattached to each other, whereby motion of the inner layer and outer layer relative to each other is not impeded thereby not restricting the flexion of the fingers of the prosthesis, and wherein the exterior surface of the outer layer is configured to resemble human skin.

30. A method according to claim 29, wherein the step of attaching the outer and inner layers to each other comprises applying adhesive to adjacent surfaces of the inner and outer layers.

31. A method according to claim 30, wherein the step of attaching the outer and inner layers comprises forming a bore in the outer layer at a location at which the inner and outer layers are to be attached and injecting the adhesive through the bore.

32. A method according to claim 29, wherein the method further comprises disposing the inner layer on a support.

33. A method according to claim 32, wherein the method further comprises disposing the outer layer over the inner layer on the support before attaching the outer and inner layers to each other at the plurality of spaced apart locations.

34. A method according to claim 29, wherein the method comprises disposing an adhesive resistant material on the outwardly directed surface of the inner layer at locations where the outer and inner layers are to be unattached to each other, the step of disposing the adhesive resistant material being carried out before the step of receiving the inner layer in the space defined by the outer layer.

* * * * *